United States Patent
Park et al.

(10) Patent No.: US 8,401,149 B2
(45) Date of Patent: Mar. 19, 2013

(54) X-RAY PHOTOGRAPHING APPARATUS FOR RECEIVING AND EDITING X-RAY IMAGE

(75) Inventors: Jong-Lae Park, Seoul (KR); Ki-Bong Sung, Goyang-si (KR)

(73) Assignee: Poskom Co., Ltd., Gyeonggi-Do (KR)

( * ) Notice: Subject to any disclaimer, the term of this patent is extended or adjusted under 35 U.S.C. 154(b) by 165 days.

(21) Appl. No.: 12/741,970

(22) PCT Filed: Nov. 20, 2008

(86) PCT No.: PCT/KR2008/006840
§ 371 (c)(1),
(2), (4) Date: May 7, 2010

(87) PCT Pub. No.: WO2009/069914
PCT Pub. Date: Jun. 4, 2009

(65) Prior Publication Data
US 2010/0246772 A1 Sep. 30, 2010

(30) Foreign Application Priority Data
Nov. 30, 2007 (KR) .................... 10-2007-0123704

(51) Int. Cl.
*H05G 1/56* (2006.01)

(52) U.S. Cl. ........................................... 378/114
(58) Field of Classification Search ................ 378/62, 378/98, 98.8, 114–116
See application file for complete search history.

(56) References Cited

U.S. PATENT DOCUMENTS
5,005,126 A * 4/1991 Haskin .............................. 378/4
2006/0008054 A1* 1/2006 Ohara ........................... 378/114

FOREIGN PATENT DOCUMENTS
| JP | 08-066393 A | 3/1996 |
| JP | 11-104117 A | 4/1999 |
| JP | 2004-188084 A | 7/2004 |
| KR | 2002-0008810 A | 1/2002 |

* cited by examiner

Primary Examiner — Courtney Thomas
(74) Attorney, Agent, or Firm — Rabin & Berdo, P.C.

(57) ABSTRACT

An X-ray imaging system includes a digital imaging panel for capturing an X-ray image of an object and an X-ray device for irradiating a beam of X-rays toward the digital imaging panel and making wireless communication with the digital imaging panel. The X-ray device is capable of directly receiving data of an X-ray image of an object from a digital imaging panel, enabling an operator to see the X-ray image on a real time basis and editing and storing the X-ray image by itself.

3 Claims, 4 Drawing Sheets

Fig. 4
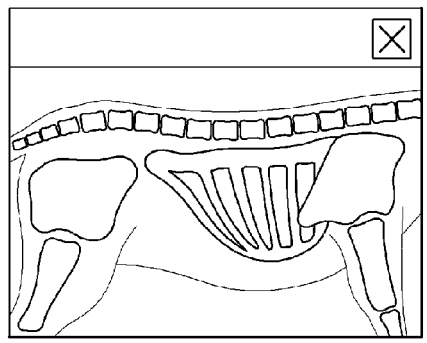
(a)
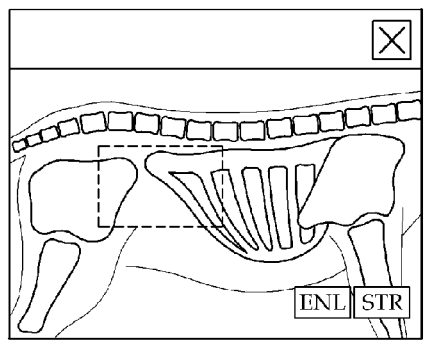
(b)
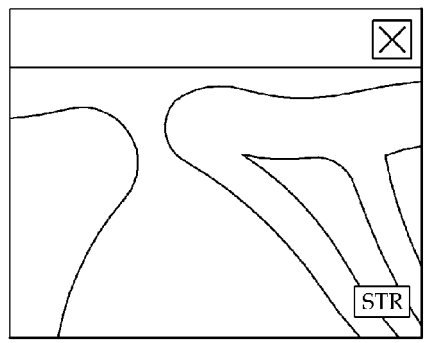
(c)
Fig. 5

X-RAY PHOTOGRAPHING APPARATUS FOR RECEIVING AND EDITING X-RAY IMAGE

TECHNICAL FIELD

The present invention relates to an X-ray imaging system and, more particularly, to an X-ray imaging system including an X-ray device capable of receiving an X-ray image captured by a digital imaging panel on a real time basis and editing or managing the received X-ray image by itself.

BACKGROUND ART

An X-ray imaging system refers to a system that helps a user diagnose the health condition of a human patient or an animal by transmitting a beam of X-rays through an object such as the human patient or the animal and capturing an X-ray image from the beam of X-rays coming out of the object. Conventional X-ray imaging systems include an X-ray device for generating a beam of X-rays and irradiating the same toward an object and an image capturing device for sensing the beam of X-rays transmitted through the object and capturing an X-ray image of the object. The image capturing device makes use of an X-ray film or a digital imaging panel in capturing the X-ray image of the object.

In case where the X-ray image is captured through the use of the X-ray film, it is necessary to replace the X-ray film with a new one each time the X-ray image of an object is captured.

A great deal of time and effort is required in developing the X-ray film. The X-ray film is stored at a specified depository and should be manually searched whenever there is a need to use the same. Thus the tasks of storing and searching the X-ray film are time-consuming and costly.

In contrast, the digital imaging panel makes it possible to see the X-ray image of an object through a management computer and to store the X-ray image at the management computer which is connected to the digital imaging panel. Use of the digital imaging panel provides an advantage in that the X-ray image stored in a specified memory space can be searched with ease.

In case of capturing the X-ray image of an object through the use of the digital imaging panel, it is possible to store a large number of X-ray images in a small memory, thanks to the rapid development of memory technology. As compared to the X-ray film requiring a wide depository for its storage, the digital imaging panel allows an operator to effectively manage and operate an X-ray imaging system.

FIG. 1 is a view for explaining a conventional X-ray imaging system that makes use of a digital imaging panel. Referring to FIG. 2, the X-ray imaging system includes a portable X-ray device 1 for generating a beam of X-rays and irradiating it toward an object 4 and an image capturing device 5 for capturing an X-ray image of the object 4. The portable X-ray device 1 is provided with a hand-held switch 3 through which a user's command is inputted to trigger irradiation of the beam of X-rays toward the object 4.

The image capturing device 5 includes a digital imaging panel 6 and a management computer 7. The digital imaging panel serves to sense the beam of X-rays transmitted through the object 4 and to convert the sensed X-ray beam to electric signals, thereby producing data of an X-ray image. The management computer 7 serves to initialize the digital imaging panel 6 prior to irradiating the beam of X-rays toward the object 4 and to display, store and manage the data of an X-ray image produced by the digital imaging panel 6. In the digital imaging panel 6, photosensitive cells for generating electric charges in an amount proportional to the sensed X-ray beam are arranged in a matrix pattern. The electric charges generated in the respective photosensitive cells are converted to electric signals. The electric signals thus converted are compared with a reference signal, thus forming the data of an X-ray image. The data of an X-ray image is supplied to the management computer 7 where the data are displayed or stored.

With the conventional X-ray imaging system, it is necessary for an operator to initially synchronize the digital imaging panel 6 with the management computer each time an X-ray image of the object 4 is taken. Using the management computer 7, the operator ascertains whether the X-ray image of the object 4 was captured correctly. Then the X-ray image is stored in the management computer 7 or discarded. In order to take the X-ray image of the object 4, the operator should keep coming and going between different places to control the operation of the X-ray device 1 and the management computer 7, which causes inconvenience to the operator.

Another problem posed in the conventional X-ray imaging system is that the management computer 7 needs to be connected to the digital imaging panel 5 in order to take the X-ray image of the object 4, which makes it difficult to carry the X-ray imaging system with the operator.

DISCLOSURE OF INVENTION

Technical Problem

Therefore, it is an object of the present invention to provide an X-ray imaging system including an X-ray device capable of directly receiving data of an X-ray image of an object from a digital imaging panel, enabling an operator to see the X-ray image on a real time basis and editing and storing the X-ray image by itself.

Technical Solution

With the above object in view, the present invention provides an X-ray imaging system, comprising: a digital imaging panel for capturing an X-ray image of an object; and an X-ray device for irradiating a beam of X-rays toward the digital imaging panel and making communication with the digital imaging panel, wherein the X-ray device includes: an X-ray irradiating unit for generating the beam of X-rays and irradiating the beam toward the digital imaging panel through the object; a synchronization control unit for generating a control signal to synchronize the digital imaging panel and the X-ray irradiating unit prior to irradiating the beam of X-rays toward the digital imaging panel; a signal sending and receiving unit for sending the control signal to the digital imaging panel and receiving data of an X-ray image of the object from the digital imaging panel; a display unit for displaying the X-ray image using the data received from the digital imaging panel; a user interface unit through which to input a user's command to edit and manage the X-ray image displayed on the display unit; and an editing unit for editing and managing the X-ray image in response to the user's command.

Advantageous Effects

The present X-ray imaging system noted above offers various advantages over the conventional X-ray imaging systems.

First, the X-ray imaging system enables the operator to directly ascertain whether the X-ray image of an object was correctly captured. This is because the X-ray device of the X-ray imaging system is capable of receiving and displaying the X-ray image of an object captured by the digital imaging panel.

Second, the X-ray imaging system possesses a function of editing and managing the X-ray image of an object in response to the operator's (user's) command inputted to the X-ray imaging system. This makes it possible for the operator to edit and use the X-ray image in many different forms depending on the usage thereof.

Third, the X-ray imaging system is capable of storing the X-ray image on a file system, which allows the operator to search a desired X-ray image with ease.

Fourth, the X-ray imaging system is provided with a dual-stage switch having a first operative position in which to synchronize the X-ray device with the digital imaging panel and a second operative position in which to trigger the image taking operation. This enables the operator to perform the synchronization operation and the image taking operation in a convenient manner.

BRIEF DESCRIPTION OF DRAWINGS

FIGS. 4A, 4B and 4C are views for specifically explaining how to edit an X-ray image.

FIG. 5 is a view for specifically explaining how to store and manage the X-ray image edited.

BEST MODE FOR CARRYING OUT THE INVENTION

Hereinafter, an X-ray imaging system in accordance with the present invention will be described in detail with reference to the accompanying drawings.

Figure 1:
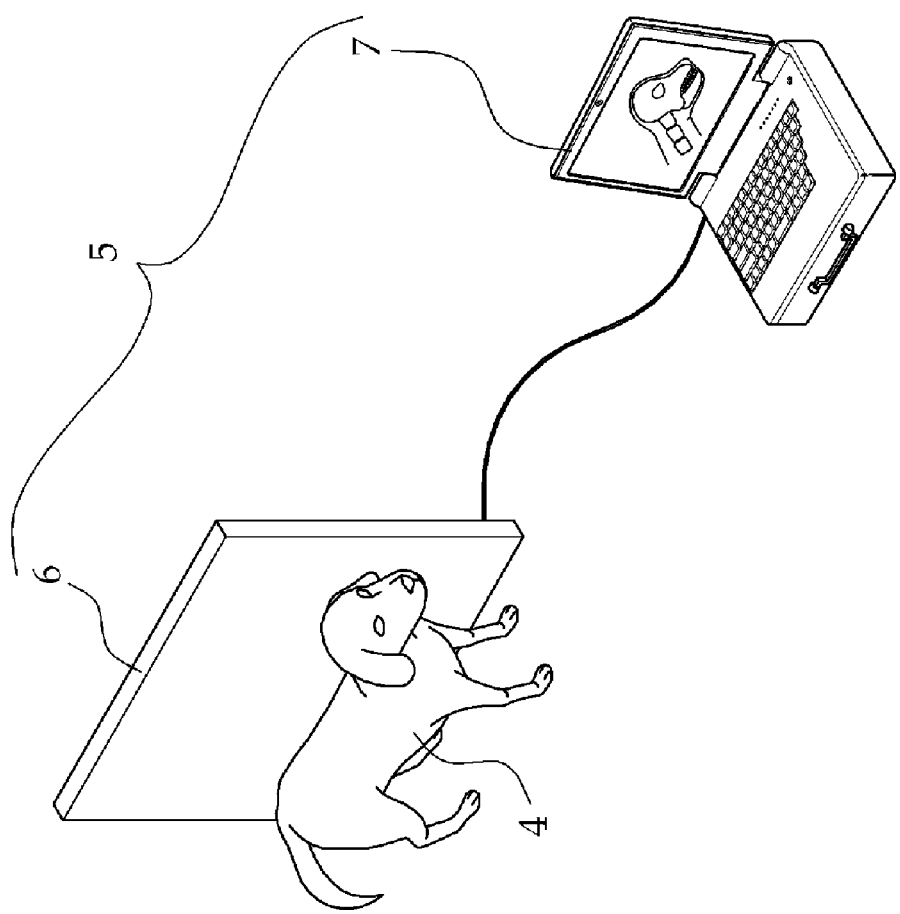
FIG. 1 is a view illustrating a conventional X-ray imaging system that makes use of a digital imaging panel.
Figure 1:
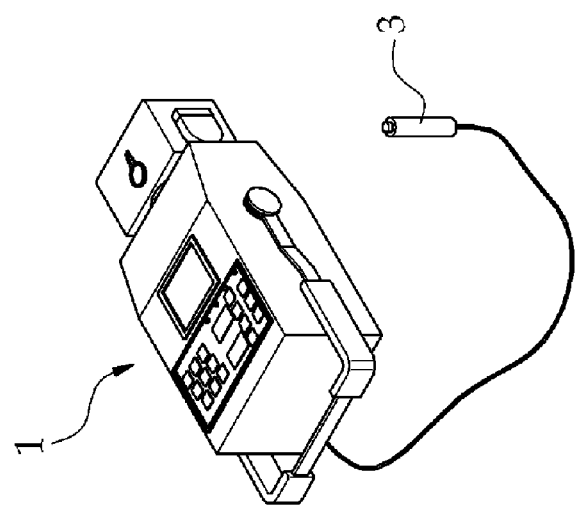
Figure 2:
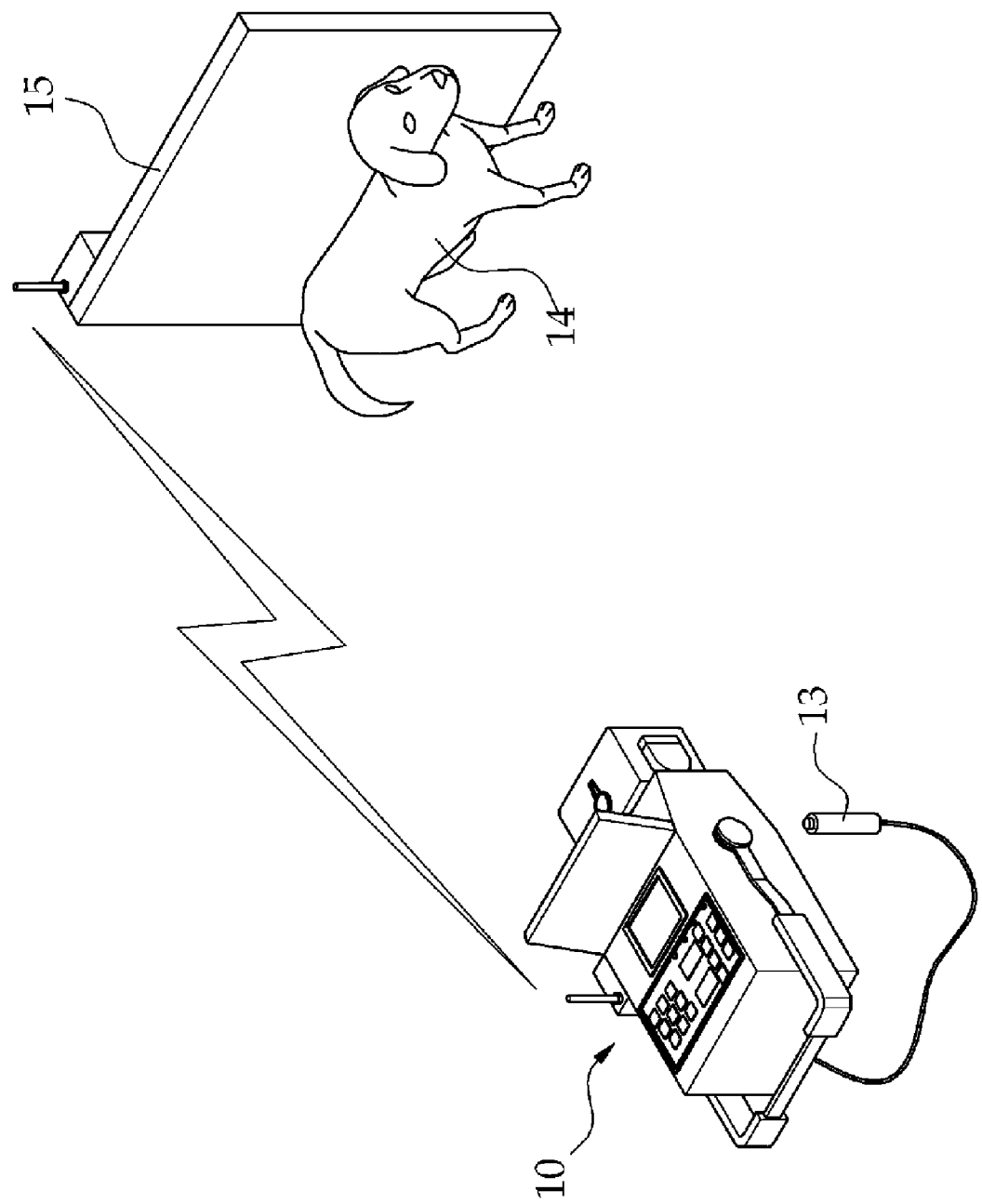
FIG. 2 is a view showing an X-ray imaging system in accordance with one embodiment of the present invention.

FIG. 2 is a view showing an X-ray imaging system in accordance with one embodiment of the present invention. Referring to FIG. 2, the X-ray imaging system of the present invention includes an X-ray device 10 for generating a beam of X-rays and irradiating it toward an object 14 and a digital imaging panel 15 for capturing an X-ray image of the object 14.

The X-ray device 10 is provided with a hand-held dual-stage switch 23 for use in inputting user's commands. The switch 13 has a first operative position in which to input a first user's command to initially synchronize the X-ray device 10 with the digital imaging panel 15 and a second operative position in which to input a second user's command to trigger irradiation of the X-ray beam toward the object 14.

In the digital imaging panel 15, photosensitive cells for generating electric charges in an amount proportional to the intensity of the sensed X-ray beam are arranged in a matrix pattern. If the digital imaging panel 15 receives the first user's command from the X-ray device 10, the electric charges generated in the photosensitive cells are initialized. If the X-ray device 10 irradiates a beam of X-rays toward the object 14 in response to the second user's command, the photosensitive cells of the digital imaging panel 15 generate electric charges in an amount proportional to the intensity of the sensed X-ray beam. The electric charges thus generated are converted to electric signals, the intensity of which is compared with a threshold value to produce digital data indicative of the X-ray image of the object 14.

The data of the X-ray image generated in the digital imaging panel 15 are transmitted to the X-ray device 10 through a wireless communication channel. Upon receiving the data of the X-ray image, the X-ray device 10 displays the X-ray image and edits and stores the X-ray image according to a user's command inputted thereto.

The Bluetooth for short-range wireless communication or an infrared communication protocol may be used in sending and receiving the control signal for synchronization and the data of the X-ray image between the X-ray device 10 and the digital imaging panel 15. Depending on the application of the present invention, it may be possible to use various kinds of wire or wireless communication protocols other than the Bluetooth and the infrared communication protocol, which should fall within the scope of the present invention.

Figure 3:
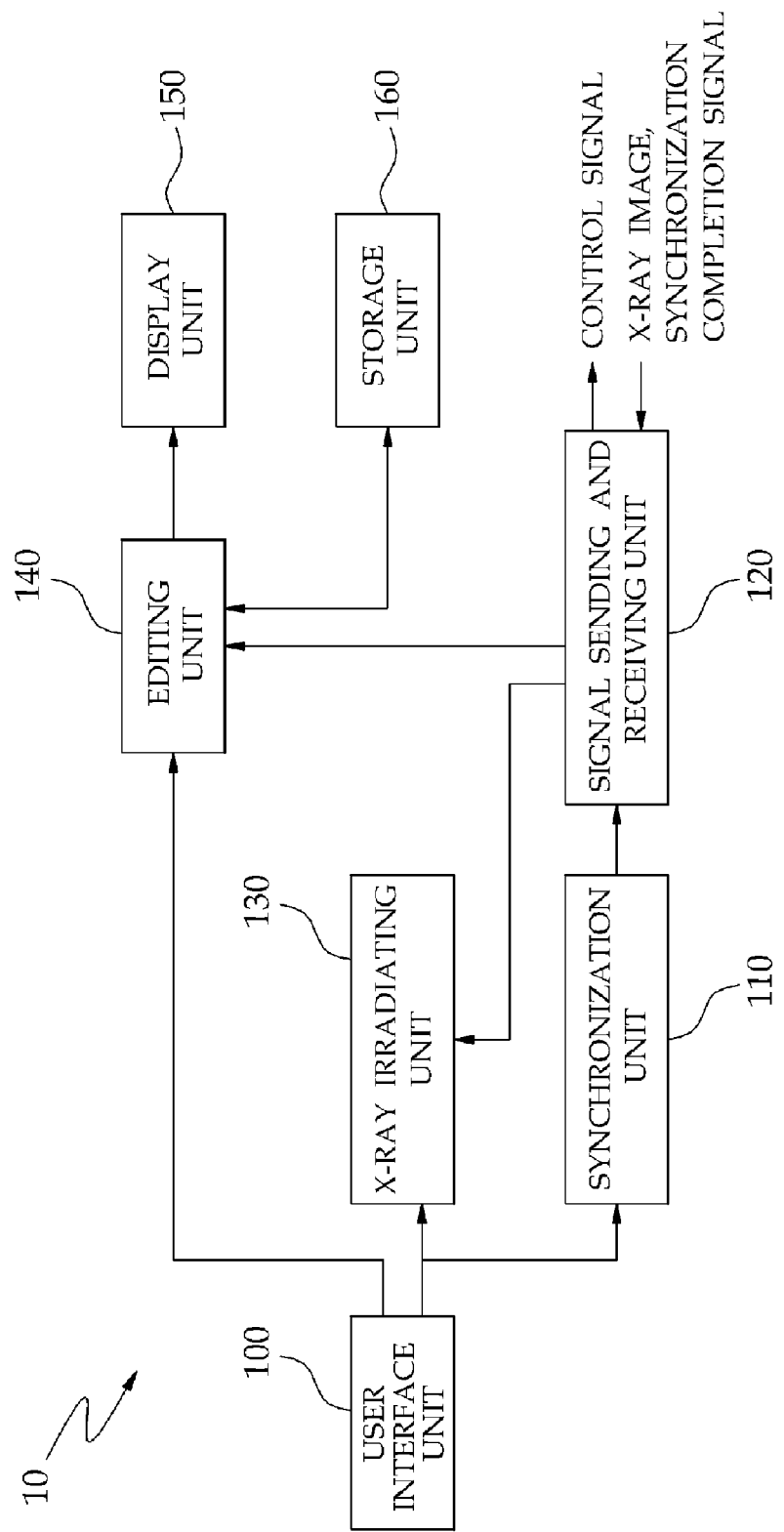
FIG. 3 is a functional block diagram showing the present X-ray imaging system in more detail.

FIG. 3 is a functional block diagram showing the present X-ray imaging system in more detail. Referring to FIG. 3, a first user's command for initially synchronizing the digital imaging panel 15 is inputted through a user interface unit 100 in order to capture the X-ray image of the object 14. Responsive to the first user's command thus inputted, a synchronization control unit 110 generates a control signal for initial synchronization of the digital imaging panel 15. The control signal is sent to the digital imaging panel 15 through a signal sending and receiving unit 120. In response to the control signal, the signal sending and receiving unit 120 receives a synchronization completion signal from the digital imaging panel 15.

If a second user's command for triggering an X-ray image capturing operation is inputted from the user interface unit 100 with the synchronization completion signal received, an X-ray irradiating unit 130 generates a beam of X-rays and irradiates it toward the object 14. If a predetermined period of time lapses after irradiation of the X-ray beam on the object 14, the signal sending and receiving unit 120 receives data of the X-ray image of the object 14 from the digital imaging panel 15. The data of the X-ray image thus received are supplied to an editing unit 140. Depending on the application of the present invention, the data of the X-ray image may be non-enciphered or non-compressed coded data or enciphered or compressed coded data.

The editing unit 140 decodes the data of the X-ray image with or without deciphering or decompressing the same and converts the decoded data of the X-ray image to a displayable format before they are supplied to a display unit 150. Responsive to a third user;s command inputted from the user interface unit 100, the editing unit 140 edits the X-ray image of the object 14 displayed and performs management, e.g., cancellation or storage, of the displayed X-ray image.

As one method of editing the displayed X-ray image, the editing unit 140 enlarges or reduces a particular portion of the X-ray image of the object 14. Another method of editing the displayed X-ray image, the editing unit 140 retrieves another X-ray image stored in a storage unit 160 and combines the same with the displayed X-ray image to produce a new X-ray image. As a further method of editing the displayed X-ray image, the editing unit 140 adds a text or an icon to a particular portion of the displayed X-ray image to produce a new X-ray image.

As one method of managing the displayed X-ray image, the editing unit 140 stores the displayed X-ray image or the edited X-ray image in the storage unit 160. Preferably, the editing unit 140 is provided with a file system that stores the displayed X-ray image or the edited X-ray image in a specified directory with an arbitrary file name. As another method of managing the displayed X-ray image, the editing unit 140 searches for an X-ray image stored in a specified directory with an arbitrary file name according to a user's command and retrieves the searched X-ray image from the storage unit 160 to display it on a display unit 150.

FIGS. 4A, 4B and 4C and FIG. 5 are views for specifically explaining how to edit an X-ray image and how to manage the X-ray image edited. Hereinafter, one specific method of editing the X-ray image will be described with reference to FIGS. 4A, 4B and 4C.

Illustrated in FIG. 4A is an X-ray image captured by the digital imaging panel 15. The region of the X-ray image to be enlarged is designated as indicated by a dot line in FIG. 4B. The region of the X-ray image to be enlarged can be designated through the use of a mouse or an electronic pen provided in the user interface unit 100 or by the user's touching a touch screen. Then the region of the X-ray image indicated by the dot line is enlargedly displayed as illustrated in FIG. 4C. An icon used to store the enlarged image together with the original X-ray image is activated on the display unit 150.

If the icon is selected through the user interface unit 100, the storage directories of the storage unit 160 and the contents of the X-ray image files stored in the directories are displayed on the display unit 150 as illustrated in FIG. 5. Then the user selects one of the directories in which the enlarged image is to be stored and stores the enlarged image in the storage unit 160 by inputting a file name and a file format.

Although one embodiment of the present invention has been described for illustrative purpose, the present invention is not limited thereto. It will be understood by those skilled in the art that various changes and modifications may be made without departing from the scope of the invention defined in the claims.

INDUSTRIAL APPLICABILITY

With the X-ray imaging system described hereinabove, the X-ray device is capable of directly receiving data of an X-ray image of an object from a digital imaging panel, enabling an operator to see the X-ray image on a real time basis and editing and storing the X-ray image by itself.

The invention claimed is:

1. An X-ray device, comprising:
   an X-ray irradiating unit for generating a beam of X-rays and irradiating the beam toward a digital imaging panel through an object;
   a synchronization control unit for generating a control signal to synchronize the digital imaging panel and the X-ray irradiating unit prior to irradiating the beam of X-rays toward the digital imaging panel;
   a signal sending and receiving unit for sending the control signal to the digital imaging panel and receiving data of an X-ray image of the object from the digital imaging panel;
   a display unit for displaying the X-ray image using the data received from the digital imaging panel;
   a user interface unit through which to input a user's command to edit and manage the X-ray image displayed on the display unit; and
   an editing unit for editing and managing the X-ray image on a file system in response to the user's command,
   wherein the X-ray device is portable,
   wherein the X-ray irradiation unit, the synchronization control unit, the signal sending and receiving unit, the display unit, the user interface unit and the editing unit are integrated into the X-ray device.

2. The X-ray device as recited in claim 1, wherein the editing unit is configured to convert a size or format of the X-ray image in response to the user's command.

3. The X-ray device as recited in claim 1, wherein the X-ray device further includes a dual-stage switch through which to input a user's command for initially synchronizing the digital imaging panel and a user's command for triggering irradiation of the beam of X-rays toward the digital imaging panel.

* * * * *